US00PP33524P2

(12) United States Plant Patent
Van Swieten

(10) Patent No.: US PP33,524 P2
(45) Date of Patent: Sep. 28, 2021

(54) ***PHALAENOPSIS* ORCHID PLANT NAMED 'PHALLINCG'**

(50) Latin Name: ***Phalaenopsis* hybrid**
Varietal Denomination: PHALLINCG

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,216

(22) Filed: Apr. 15, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHALLINCG', particularly characterized by reddish-purple, striped flowers with light purple edges and dark red and reddish-purple lips, flowers with a flat shape in lateral view, dorsal sepals with an incurving curvature of the longitudinal axis, and is propagated by meristem tissue culture, is disclosed.

3 Drawing Sheets

Genus and species: *Phalaenopsis* hybrid.
Variety denomination: 'PHALLINCG'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALLINCG'.

The new *Phalaenopsis* plant is a product of a planned breeding program conducted by the inventor in Bleiswijk, the Netherlands. The objective of this breeding program was to create a new *Phalaenopsis* plant with reddish-purple, striped flowers with light purple edges and dark red and reddish-purple lips, suitable for potted plant production.

The new *Phalaenopsis* plant 'PHALLINCG' is a result of cross-pollination made by the inventor in April 2012 in Bleiswijk, the Netherlands, of the proprietary female, or seed parent, *Phalaenopsis* hybrid 'PHALUFREL' (U.S. Plant Pat. No. 29,259) with the proprietary male, or pollen parent, *Phalaenopsis* hybrid '32522-04' (unpatented).

The new *Phalaenopsis* was selected by the inventor as a single plant within the progeny of the stated cross-pollination in a controlled greenhouse in Bleiswijk, the Netherlands, in June 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0286), by Applicant who obtained the subject matter disclosed directly from the inventor. 'PHALLINCG' has not been made publicly available or sold anywhere in the world prior to the effective filing date of this application with the exception of sales or disclosures made one year or less before the effective filing date of this claimed invention by Applicant who obtained 'PHALLINCG' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALLINCG' as a new and distinct variety of *Phalaenopsis* plant:

1) Reddish-purple, striped flowers with light purple edges and dark red and reddish-purple lips;
2) Flower shape in lateral view is flat; and
3) Dorsal sepal curvature of longitudinal axis is incurving.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2021. Colors in the photographs may differ from the color values cited in the detailed botanical description, which accurately describe the actual colors of the new variety.

DESCRIPTION OF THE NEW VARIETY

Figure 1:
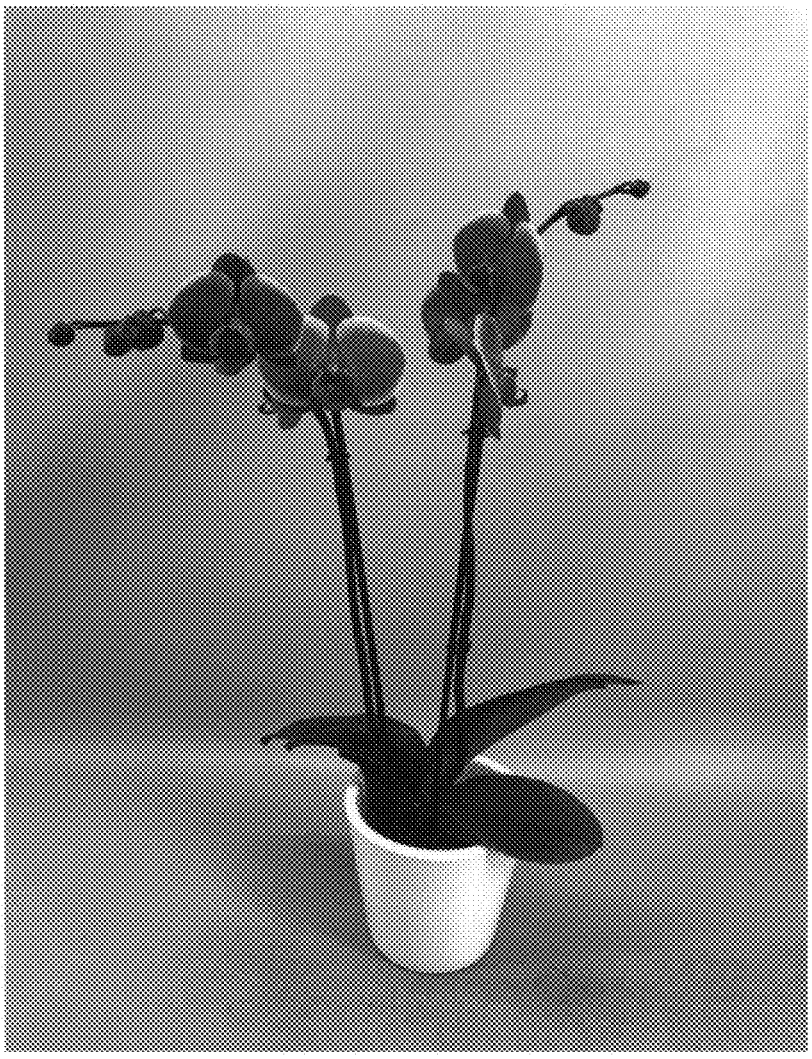
FIG. 1 shows the overall plant habit, including blooms, buds, and foliage of 'PHALLINCG'.
Figure 2:
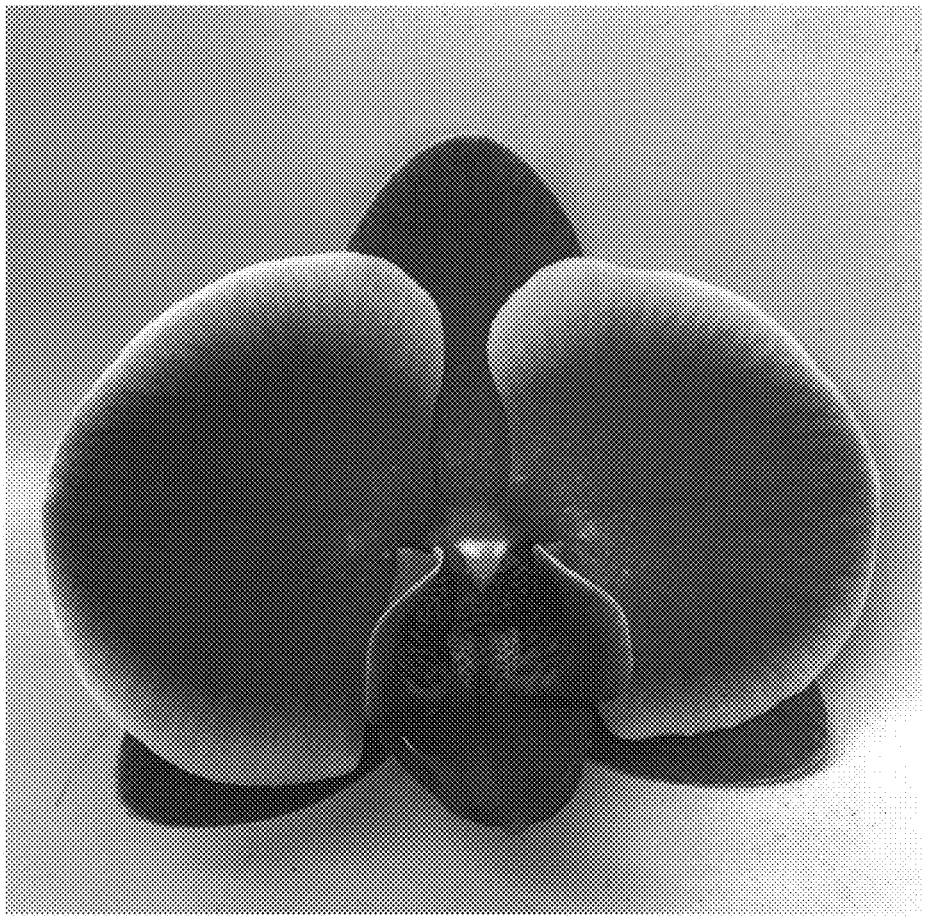
FIG. 2 shows a close-up of a flower of 'PHALLINCG'.
Figure 3:
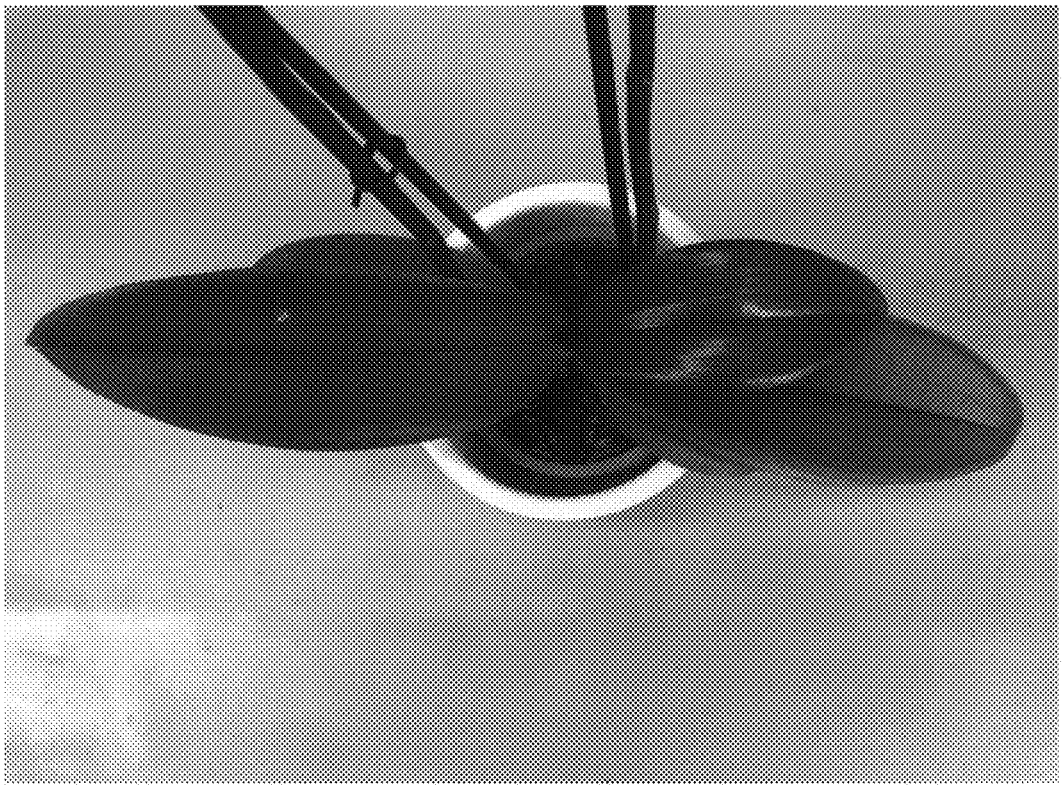
FIG. 3 shows an overhead view of the leaves of 'PHALLINCG'.

The following detailed description sets forth the distinctive characteristics of 'PHALLINCG'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALLINCG'.

Parentage:

*Female parent*.—*Phalaenopsis* cultivar 'PHALUFREL' (U.S. Plant Pat. No. 29,259).

*Male parent*.—*Phalaenopsis* cultivar '32522-04' (unpatented).

Propagation:

*Type*.—Meristem tissue culture.

Roots:

*Root description*.—Greyed-green (a color in between RHS 190B and RHS 190C) colored roots with branching lateral roots having yellow-green (a color in between RHS N144A and RHS 145C) with a touch of purplish-red (a mix of RHS N77B and RHS N79C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme inflorescence.

*Height* (*from soil level to top of inflorescence*).—Approximately 55.0 cm to 60.0 cm.

*Width* (*measured from leaf tips*).—About 36.0 cm to 38.0 cm.

*Vigor*.—Strong.

Leaves:

*Mature leaves*.—Quantity per plant: 7 to 8 leaves are produced before flowering. Length (fully expanded): 19.0 cm to 21.0 cm. Width: 7.0 cm to 8.0 cm. Position of the broadest part of the leaf: At the middle. Shape: Oblong. Base shape: Moderately elongated. Apex: Obtuse unequal. Leaf blade angle with the petiole (measured from the horizontal position): Between 10 degrees and 35 degrees. Leaf margin: Entire. Color: Upper surface: RHS 146A with a hint of diluting dark red (RHS 187A) at the base and dark red margin (RHS 187B). Lower surface: RHS 146B and dark red (RHS 187A); dark red margin (RHS 187B). Texture (both upper and lower surfaces): Smooth. Thickness: 2.0 mm to 3.0 mm. Variegation: Absent. Venation: Pattern: Parallel. Color of the midvein: Upper surface: RHS 187A. Lower surface: RHS 187B.

Peduncle:

*Quantity per plant*.—1 to 2.

*Number of flowers per peduncle*.—7 to 9.

*Length*.—55.0 cm to 60.0 cm.

*Diameter*.—6.0 mm to 7.0 mm.

*Strength*.—Strong.

*Aspect*.—Upright to slightly pendent.

*Texture*.—Smooth.

*Color*.—Dark reddish-brown (RHS 200A).

*Internode length*.—4.0 cm to 6.0 cm.

Inflorescence description:

*Appearance*.—Upright to slightly pendent, raceme inflorescence with bilaterally symmetrical flowers that open in succession beginning with the lowermost flower.

*Number of inflorescences*.—1 to 2.

*Inflorescence size*.—Height (from base to tip): 180.0 mm to 230.0 mm.

*Flowering time*.—First flowers can be expected 10 to 11 months after planting in a 12-cm pot.

*Flower*.—Height: 73.0 mm to 78.0 mm. Diameter: 85.0 mm to 90.0 mm. Depth of lip: 21.0 mm to 23.0 mm.

*Flower longevity*.—On the plant: 16 to 18 weeks.

*Flower shape*.—Flat.

*Fragrance*.—Absent.

*Flower bud*.—Average size: Large. Length: 23.0 mm to 25.0 mm. Width: 23.0 mm to 25.0 mm. Shape: Egg shaped. Color: Dark purplish-red (RHS N79C) and purplish-red (RHS N77B).

*Petals*.—Arrangement: Open/free. Shape: Semi-circular. Apex: Rounded asymmetric. Margin: Weakly undulated. Length (from base to tip): 38.0 mm to 40.0 mm. Width: 54.0 mm to 56.0 mm. Position of the broadest part of the petal: Toward the base. Color (when fully opened): Upper surface: Basic color: Reddish-purple (RHS N78A). Over color: Light purple dots (RHS 76A) at the base and light purple edge (from RHS 76A to RHS 76B toward margin); stripes (a color in between RHS N79C and N78A). Lower surface: Basic color: Reddish-purple (RHS N78B). Over color: Diluting stripes (RHS N78B) and purplish-pink shade (RHS N78C); light purple edge (from RHS 76A to RHS 76B toward margin). Number of spots and stripes on the petals (upper surface): Many stripes. Color of spots and stripes on the petals (upper surface): A color in between RHS N79C and RHS N78A. Density of netting of the petals (upper surface): None. Color of the netting (upper surface): Not applicable.

*Dorsal sepal*.—Shape: Broad elliptic. Apex: Obtuse symmetric. Margin: Entire. Length (from base to tip): 40.0 mm to 42.0 mm. Width: 28.0 mm to 30.0 mm. Position of the broadest part of the dorsal sepals: At the middle. Color (when fully opened): Upper surface: Basic color: Reddish-purple (RHS N78A). Over color: Stripes and netting (a color in between RHS N79C and RHS N78A). Lower surface: Basic color: Reddish-purple (RHS N78A). Over color: Light yellow-green (RHS 145C) and diluting reddish-purple stripes (RHS N78A). Number of spots and stripes on the dorsal sepals (upper surface): Medium stripes. Color of spots and stripes on the dorsal sepals (upper surface): A color in between RHS N79C and RHS N78A. Density of netting of the dorsal sepals (upper surface): Low. Color of the netting: A color in between RHS N79C and RHS N78A.

*Lateral sepals*.—Shape: Ovate. Apex: Obtuse symmetric. Margin: Entire. Length (from base to tip): 40.0 mm to 42.0 mm. Width: 28.0 mm to 30.0 mm. Position of the broadest part of the lateral sepals: At the base. Color (when fully opened): Upper surface: Basic color: Reddish-purple (RHS N78A). Over color: Light yellow-green (RHS 145C) and dotted (RHS N79C) at the base; striped (a color in between RHS N79C and RHS N78A); white margin (RHS NN155C) at the tip. Lower surface: Basic color: Reddish-purple (RHS N78B). Over color: Light yellow-green (RHS 145C); reddish-purple midvein (a color in between RHS N78A and RHS NN78A) toward the tip. Number of spots, dots, and stripes on the lateral sepals (upper surface): Medium dots and medium stripes. Color of spots, dots, and stripes on the lateral sepals (upper surface): Dots (RHS N79C) and stripes (a color in between RHS N79C and RHS N78A). Density of netting of the lateral sepals (upper surface): Medium. Color of the netting (upper surface): A color in between RHS N79C and RHS N78A.

*Labellum* (*lip*).—Whiskers: Present. Length of whiskers: 8.0 mm to 10.0 mm. Color of whiskers: Dark purplish-red (RHS N79C) with small white tips (RHS NN155C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Entire. Length: 20.0 mm to 22.0 mm. Width: 15.0 mm to 17.0 mm. Color: Upper surface: Yellowish-green (RHS 156C) and dark red stripes (RHS 59A) at the base; dark red (RHS 183B) toward margin on one side; reddish-purple (RHS N78A) toward other margin and the tip. Lower surface: Yellowish-green (RHS 156B) at the base toward margin on one side and purplish-red (RHS 71A) on the other side; dark red (RHS 183A) toward margin on the other side; reddish-purple (RHS N78A) toward the tip. Number of spots and stripes on the lateral lobe: Few to medium stripes. Color of spots and stripes on the lateral lobe: RHS 59A. Density of netting of the lateral lobe: None. Color of the netting: Not applicable.

*Apical lobe*.—Shape: Triangular. Margin: Entire. Length: 19.0 mm to 21.0 mm. Width: 21.0 mm to 23.0 mm. Color: Upper surface: Dark red (RHS 187C) at the base and reddish-purple (RHS N78A) toward whiskers. Lower surface: Light reddish-purple (RHS N78D) at the middle from base toward whiskers; purplish-red wings (RHS 187D); reddish-purple margin (RHS N78A) toward the tip. Number of spots and stripes on the apical lobe: None. Color of spots and stripes on the apical lobe: Not applicable. Density of netting of the apical lobe: None. Color of the netting: Not applicable.

*Callus*.—Average size: Medium to large. Height: 8.0 mm to 9.0 mm. Length: 6.0 mm to 7.0 mm. Width: 4.0 mm to 5.0 mm. Color: Yellow front (RHS 13A); light yellow tips (RHS 10B); dark red stripes and dots (RHS 59A).

Reproductive organs:

*Column*.—Length: 8.0 mm to 10.0 mm. Diameter: 5.0 mm to 6.0 mm. Color: Reddish-purple (RHS N78A).

*Pollinia*.—Quantity: 2. Diameter: 0.9 mm to 1.1 mm. Color: Orange (RHS 24A).

*Ovary*.—Length: 11.0 mm to 13.0 mm. Diameter: 2.2 mm to 2.5 mm.

*Pedicel*.—Length: 35.0 mm to 37.0 mm. Diameter: 2.8 mm to 3.2 mm. Color: Purplish-red (RHS N77B) with a touch of yellow-green (RHS 146D) and purplish-pink (RHS N78C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALLINCG' differs from the female parent plant 'PHALUFREL' (U.S. Plant Pat. No. 29,259) in that 'PHALLINCG' has oblong leaves and broad elliptic dorsal sepals, whereas 'PHALUFREL' has obovate leaves and elliptic dorsal sepals.

'PHALLINCG' differs from the male parent plant '32522-04' (unpatented) in that 'PHALLINCG' has columns that are reddish-purple and apical lobes that are dark red and reddish-purple toward whiskers, whereas '32522-04' has columns that are purplish-pink and apical lobes that are red and reddish-purple toward whiskers.

'PHALLINCG' is most similar to the commercial *Phalaenopsis* plants named 'PHALOSZIH' (U.S. Plant Pat. No. 29,945) and 'PHALHITWOQ' (U.S. Plant Pat. No. 32,283). 'PHALLINCG' differs from the commercial variety 'PHALOSZIH' in that 'PHALLINCG' has obtuse dorsal sepal apexes and dark purplish-red whiskers with small white tips, whereas 'PHALOSZIH' has rounded to slightly emarginated dorsal sepal apexes and dark red whiskers.

'PHALLINCG' differs from the commercial variety 'PHALHITWOQ' in that 'PHALLINCG' has smaller flowers, smaller lip depth, and wider apical lobes than 'PHALHITWOQ'.

I claim:

1. A new and distinct variety of *Phalaenopsis* plant named 'PHALLINCG', substantially as described and illustrated herein.

* * * * *